United States Patent [19]

Bennett

[11] Plant 5,069

[45] Jul. 19, 1983

[54] MINIATURE ROSE PLANT

[76] Inventor: Cecilia L. D. Bennett, 489 Minot Ave., Chula Vista, Calif. 92010

[21] Appl. No.: 342,711

[22] Filed: Jan. 25, 1982

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant characterized by the rich pink blend of the bloom and distinctive plant growth.

1 Drawing Figure

1

The present invention relates to a new and distinct variety of a hardy, dwarf, miniature bush plant of the miniature class; the variety being primarily characterized as a pink blend, similar in coloring to Tiffany, a hybrid tea U.S. Plant Pat. No. 1,304. Introduced by Howard Rose Co., in 1954.

The variety is further characterized by:

An abundance of blooms, usually blooming in clusters of five or more.

A strong fragrance of fresh apples.

A plant which is bushy, compact, well foliaged, small glossy foliage; buds and flowers are comparable in size to Tea Party, a miniature introduced by Sequoia Nursery in 1972.

The plant ranges in height from 12 to 15 inches. Grows well in greenhouse or outdoors; makes a very attractive plant for containers.

The present variety of miniature rose was originated by me at Tiny Petal's Nursery, located at Chula Vista, Calif., under careful observation, and is a cross of "Little Chief" a miniature as the pollen parent, introduced by Mini Roses and Sequoia Nursery in 1971, and "Electron" a hybrid tea (U.S. Plant Pat. No. 3,226.) as the seed parent.

Subsequent to origination of the variety I successfully reproduced it by cuttings and bud-grafts at Tiny Petal's Nursery located at aforesaid with reproductions coming true in all respects.

The color photographs illustrate the variety. Referring now specifically to the new and distinct variety of miniature rose plant, the following is a detailed description thereof in outline, all major color plate identification being by reference to The British Colour Council Horticultural Colour Chart.

Type: Hardy; dwarf; compact, seedling; greenhouse; outdoors; cut flowers; garden decoration; potted plant.

Class: Miniature;

*Variety name.*—"Dominique".

Flowers borne: One to a stem with clusters of three, five and more as plant grows larger.

Quantity of bloom: Abundant both inside the hothouse or outdoors.

Bud:

*Peduncle.*—Slender; erect; slight tinge of red; ¾ to 1 inch in length.

*Hairs.*—Very minute; reddish. Before calyx breaks; size small. Form short; roundish with a little foliating of appendages. Appendages barely clearing the tip of the bud.

*Color.*—Medium green with a slight tinge of red.

*As calyx breaks.*—Color — medium pink with a slight tinge of green at the base of petal. Opens well in all weather.

Bloom:

*Size when fully open.*—Medium, averaging 1½ to 1¾ inches in diameter.

*Petalage.*—Double — averaging about 35 to 40 petals, arranged regularly.

*Form.*—High centered circular form. Opens slowly, petals reflex very slightly. Open flower reveals stamens.

Petals: Medium substance; matt surface on topside and underside of petals.

*Shape.*—Outside petals, broad lanceolate with acute tip; intermediate petals, medium lanceolate with acute tip; inside petals, arrow shaped with acute tip.

Color: Newly opened flower from a flower as grown at Chula Vista, Calif.:

*Outer petals.*—Outside surface — 621/3 page 183 with base of petal tipped in mimosa yellow 602/2 page 143 of The British Colour Council Horticultural Colour Chart.

*Outer petals.*—Topside surface — the same as outer surface.

*Intermediate petals.*—Outer surface — 621/2 page 183 with base of petal tipped in mimosa yellow 602/2 page 143.

*Intermediate petals.*—Topside surface — the same as outer surface.

*Inner petals.*—Topside surface — 621/1 page 183 with base of petal tipped in mimosa yellow 602/2 page 143.

*Inner petals.*—Outer surface — the same as topside surface.

Behavior: Opens well in all weather. Form exhibition; color long lasting. Does not change color as bloom ages. Bloom will hold its form and color for a week or more.

Reproductive organs:

*Stamens.*—Abundant, arranged evenly around the pistil.

*Filaments.*—Varying lengths.

*Anthers.*—Well formed.

*Pollen.*—A generous amount.

*Pistil.*—About 20–25.

*Styles.*—Short, irregular.

*Ovaries.*—All encased in calyx.

*Hips.*—In most cases a hip is set.

*Sepals.*—Spear shaped.

*Seed.*—Usually hips produce a few seeds.

Foliage:

*Leaves.*—Compound of five, small; glossy.

*Leaflets.*—Shape: broad, roundish. Margin very serrated.

*Color.*—Medium green with no margin color change except during the fall when edge turns reddish.

Rachis: Medium length; underside smooth.

*Stipules.*—Medium length; narrow to medium width.

Growth:

*Habit.*—Dwarf, bushy, much branched.

*Growth.*—Vigorous.

*Canes.*—Medium, slender, sturdy.

*Main stem.*—Color: medium green.

*Thorns.*—Small; slender; hooked downward; greyish.

*Prickles.*—None.

*Branches.*—Color: medium green. Thorns: very sparse.

The miniature rose plant and its flowers as herein described may vary in slight detail due to climatic, soil and cultural conditions under which the variety may be grown; the present description being of the variety as grown at Chula Vista, Calif.

I claim:

1. A new and distinct variety of miniature rose plant of hardy, dwarf, bushy, much branched habit, substantially as illustrated and described, characterized by buds and flowers similar in coloring to the variety Tiffany a hybrid tea.

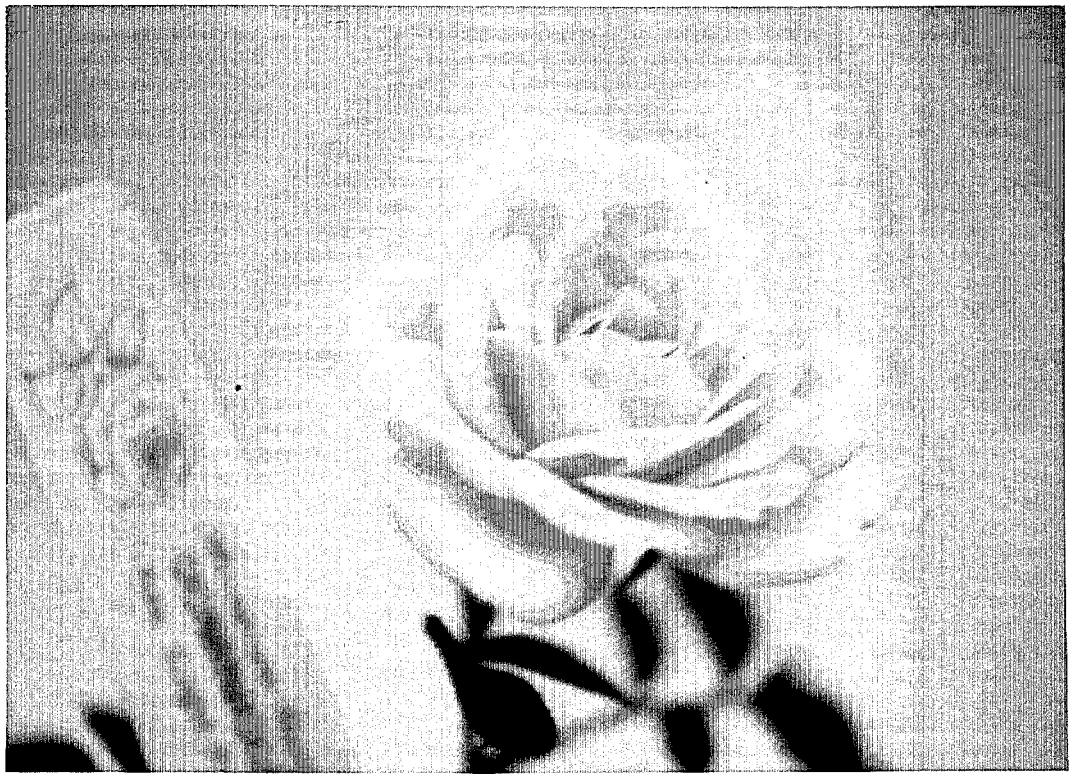

* * * * *